(12) United States Patent
Binz et al.

(10) Patent No.: US 6,780,420 B1
(45) Date of Patent: *Aug. 24, 2004

(54) CARRIER PROTEIN HAVING AN ADJUVANT EFFECT, IMMUNOGENIC COMPLEX CONTAINING IT, PROCESS FOR THEIR PREPARATION, NUCLEOTIDE SEQUENCE AND VACCINE

(75) Inventors: Hans Binz, Beaumont (FR); Thierry Baussant, Bellgarde (FR); Jean-François Haeuw, St Julien en Genevois (FR); Thien Nguyen Ngoc, St Julien en Genevois (FR)

(73) Assignee: Pierre Fabre Medicament, Boulogne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/679,750

(22) Filed: Oct. 5, 2000

Related U.S. Application Data

(63) Continuation of application No. 08/836,500, filed as application No. PCT/FR95/01463 on Nov. 7, 1995, now Pat. No. 6,197,929.

(30) Foreign Application Priority Data

Nov. 7, 1994 (FR) .............................. 94 13306

(51) Int. Cl.$^7$ ...................... A61K 39/108; A61K 39/02; A61K 45/00; A61K 39/385; C07K 1/00
(52) U.S. Cl. ............................. 424/259.1; 424/278.1; 424/234.1; 424/282.1; 424/184.1; 424/190.1; 424/193.1; 424/192.1; 424/194.1; 424/197.1; 424/196.11; 424/201.1; 530/350; 530/300; 530/806; 530/807; 530/825; 514/2
(58) Field of Search .................... 530/350, 300, 530/825, 806, 807; 424/278.1, 234.1, 259.1, 282.1, 184.1, 190.1, 193.1, 192.1, 194.1, 197.11, 196.11, 201.1; 514/2

(56) References Cited

U.S. PATENT DOCUMENTS 6,019,982 A * 2/2000 Clements et al. ........ 424/236.1

6,197,929 B1 * 3/2001 Binz et al. ................. 530/350

FOREIGN PATENT DOCUMENTS

| FR | 2 718 452 | * 10/1995 |
|---|---|---|
| WO | WOA89 05823 | 6/1989 |
| WO | WOA92 04375 | 3/1992 |
| WO | WOA93 14207 | 7/1993 |
| WO | WOA95 27787 | 10/1995 |
| WO | WO 9614415 | 5/1996 |

OTHER PUBLICATIONS

Sambrook et al. In: Molecular Cloning, A Laboratory Manual. Second Edition, Cold Spring Harbor, pp. 17.1–17.44, 1989.*

Campbell AM. In: Monoclonal Antibody Technology. Elsevier Science Publishers, The Netherlands, Chapter 1, pp. 1–32, 1984.*

Lazar et al. Mol. Cellular Biol. 8: 1247–1252, 1988.*

Merle–Poitte Merle. Doctoral Thesis Abstract, 1995–11, p. 132, 1995, abstract.*

Burgess et al. J. Cell Biol. 111: 2129=2138, 1990.*

Lawrence, J. G. et al., 'Molecular and evolutionary relationships among bacteria', J. of General Microbiology, vol. 137 No. 8, pp. 1911–1921, 1991.

Haeuw et al. Eur. J. Biochem. 255: 446–454, 1988.

Bizzini et al. Asian Pac, J. Allergy Immunol. 2: 144–153, 1984.

Bizzini et al. Biomed. Pharmacother. 46: 491–494, 1992.

* cited by examiner

*Primary Examiner*—S. Devi
(74) *Attorney, Agent, or Firm*—Wood, Phillips, Katz, Clark & Mortimer

(57) ABSTRACT

The invention relates to an adjuvant product which is intended to improve the activity of a molecule when administered to a host, characterized in that it comprises at least one part of the P40 protein of *Klebsiella pneumoniae* or a protein having at least 80% homology with the P40 protein of *Klebsiella pneumoniae*. The invention also relates to nucleotide sequences which encode these peptides or proteins and to the use of these sequences as a medicament. More particularly, such DNA sequences can be used in compositions which are intended for immunization by the intramuscular or intradermal route.

11 Claims, 6 Drawing Sheets

Figure 1:
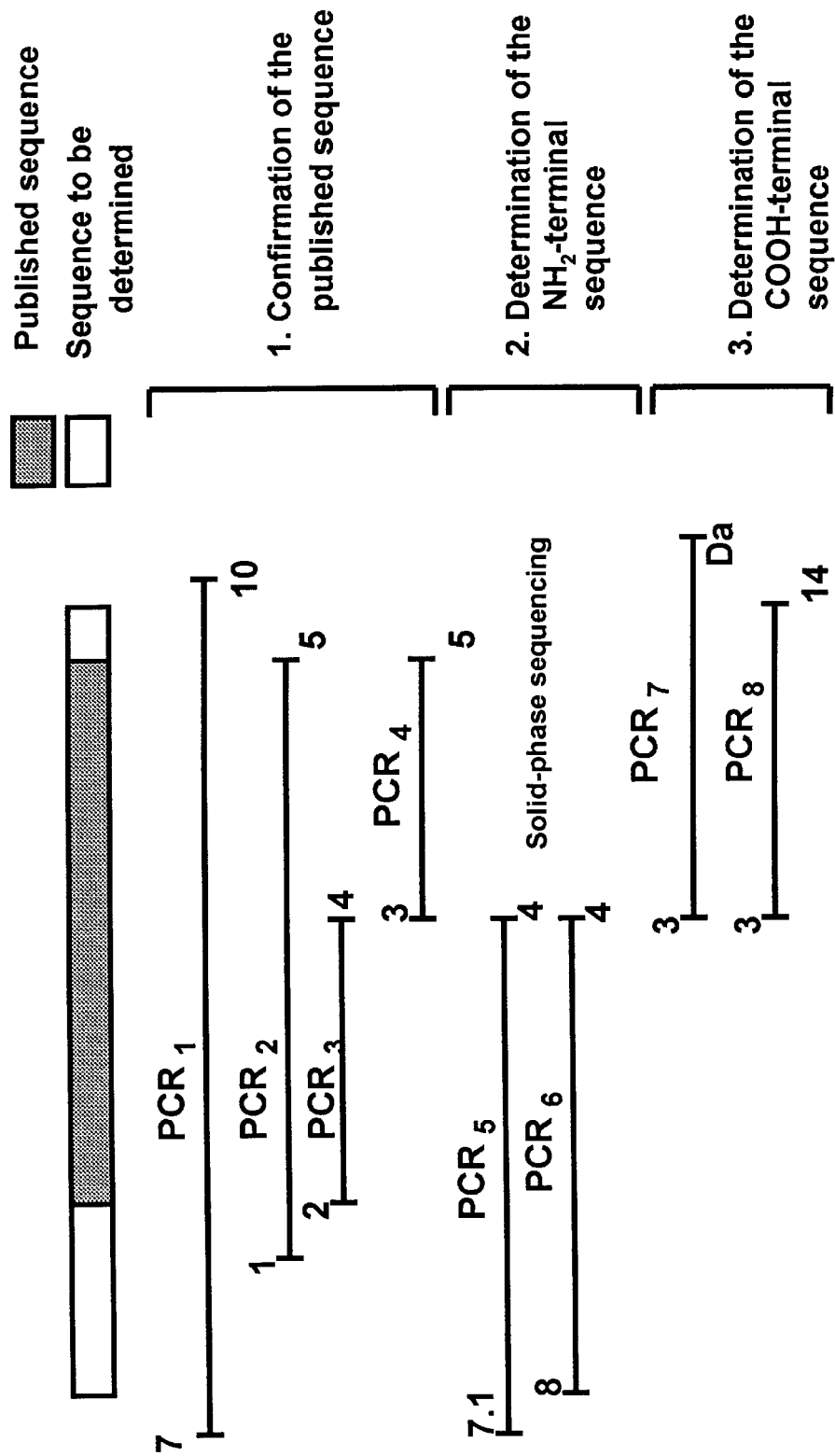

CARRIER PROTEIN HAVING AN ADJUVANT EFFECT, IMMUNOGENIC COMPLEX CONTAINING IT, PROCESS FOR THEIR PREPARATION, NUCLEOTIDE SEQUENCE AND VACCINE

This application is a Continuation of application Ser. No. 08/836,500, filed Aug. 11, 1997, which is a national stage 371 application of the international application, PCT/FR95/01463, filed Nov. 7, 1995, now U.S. Pat. No. 6,197,929, which claims foreign priority to application 94,13306 filed Nov. 7, 1994 in France.

The present invention relates to adjuvants which are intended to be attached to a molecule in order to improve its activity, in particular to increase the strength of the immune response. It also relates to complexes which contain such an adjuvant attached to an active molecule.

The active molecule can, in particular, be a protein, a peptide, a polysaccharide, an oligosaccharide or a DNA or RNA nucleic acid.

The development of vaccines which are perfectly defined and which lack pronounced side effects requires the use of immunizing antigens of low molecular weight such as peptides or oligosaccharides. These antigens of low molecular weight, and also certain antigens of higher molecular weight, such as bacterial wall polysaccharides, cannot, on their own, induce a lasting, powerful immune response. It is essential to link these antigens to carrier proteins by chemical means or by using genetic manipulation.

The carrier proteins which are currently employed are of two types:
  tetanus and diphtheria toxoids: too frequent use of these carrier proteins risks jeopardizing a strong response to the hapten and risks the possibility of problems with immunotoxicity,
  a membrane protein extract from *Neisseria meningitidis* (OMPC): consists of a membrane protein which is contaminated with lipids and LPS.

Patent EP-267 204 proposed using a support molecule which is intended to be coupled to an immunogen and which consists of an *E. coli* or salmonella membrane protein.

The Applicant has demonstrated that a protein which is extracted from the outer membrane of *Klebsiella pneumoniae* considerably improves the immune response to an antigen or a hapten when it is administered to a host at the same time as the latter. More particularly, an OmpA protein, the P40 protein of *K. pneumoniae*, can be used as an adjuvant in immunogenic complexes when it is attached to an immunogenic element.

The chemical conjugates which are derived by coupling peptides to the P40 give good results, and an assessment of the immune response shows antibody responses to these peptides which are greater than those which are observed when KLH or TT reference carrier proteins are used.

However, the peptide antigens are preferentially attached to the C-terminal part of the sequence, which is the most immunogenic part of the molecule (Puohiniemi, R et al., 1990, Infect Immu. 58, 1691–1696). This can present a serious problem in the case of fusion proteins which contain the complete P40 sequence. Therefore, use of a fragment of the sequence which supports the adjuvant activity would have a greater effect in minimizing the immunogenicity of the carrier protein and the risks associated with this immunogenicity.

For this reason, the present invention relates to an immunogenic complex of the type which comprises an immunogenic element which is attached to an adjuvant which increases the strength of the immune response, characterized in that the immunogenic element is an antigen or a hapten, and in that the adjuvant comprises at least a part of the P40 protein of *Klebsiella pneumoniae* or a protein which exhibits at least 80% homology, and preferably at least 90% homology, with the P40 protein.

In particular, the invention relates to an adjuvant which consists of a protein or a peptide having the P40 sequence which is substantially devoid of the immunogenic parts.

These P40 fragments according to the invention are, in particular:
  the P40 sequence which lacks the immunogenic periplasmic C-terminal part,
  a sequence which contains the third and the fourth extramembrane loops flanking an intramembrane sequence,
  a sequence which contains one invariant extramembrane loop and the adjacent intramembrane sequence.

Those P40 sequences are defined as invariant extramembrane loops which are homologous with the sequences of the loops which are conserved between different enterobacterial species. The sequences of the extramembrane loops which are not conserved during the course of evolution are termed variable loops. The extramembrane loops are located in accordance with the Vogel and Jahnig model (1986, J. Mol. Biol., 190: 191–199), which relates to *E. coli* OmpA.

The choice of the fragments and, more particularly, the third sequence (amino acids 127 to 179) is based on the hypothesis according to which the invariant extramembrane loops (conserved between the OmpAs of the different enterobacteria) contain sequences which are recognized by immunocompetent cells, with these latter being able to have receptors which recognize these sequences.

The specific recognition of these sequences by antigen-presenting cells would make it possible to target antigens towards these cells and thus to induce an adjuvant effect.

For this reason, the invention also relates to an adjuvant product which consists of the sequence encompassed between amino acids 1 to 179 of the P40 protein of *K. pneumoniae,* or to a sequence which exhibits at least 80%, and preferably at least 90%, homology with the sequence which is encompassed between amino acids Nos. 1 and 179 of the sequence of the P40 protein of *K. pneumoniae.*

The invention furthermore relates to an adjuvant which consists of the sequence which is encompassed between amino acids 108 to 179 of the P40 protein of *K. pneumoniae,* or to a sequence which exhibits at least 80% homology, and preferably at least 90% homology, with the sequence which is encompassed between amino acids nos. 108 and 179 of the P40 protein of *K. pneumoniae.*

According to another aspect, the invention relates to an adjuvant which consists of the sequence which is encompassed between amino acids nos. 127 to 179 of the P40 protein of *K. pneumoniae,* or to a sequence which exhibits at least 80%, and preferably at least 90%, homology with the sequence which is encompassed between amino acids nos. 127 to 179 of the P40 protein of *K. pneumoniae.*

The sequences ID No. 2, ID No. 4, ID No. 6 and ID No. 8 correspond to adjuvants according to the invention. This protein, and these peptide adjuvants, can, in particular, be prepared from membranes of bacteria of the species *Klebsiella pneumoniae*. The process then comprises the following steps:
  a) precipitating the lipopolysaccharides by adding detergent and a salt of a divalent cation, and recovering the supernatant,
  b) precipitating the proteins from the supernatant and resuspending the sediment, c) chromatographing the suspension on an anion exchanger and recovering the fractions which contain the adjuvant product, d) chromatographing on a cation exchanger and recovering the fraction which contains the adjuvant product, e) concentrating the fraction obtained from step d) in order to recover an adjuvant product in the form of protein or peptide which is essentially free of liposaccharides.

Dialysis steps can advantageously be interposed between steps b) and c), and steps c) and d), respectively.

The invention also relates to immunogenic complexes which can be obtained using the different adjuvants.

The adjuvant can be attached to the immunogenic element by chemical coupling.

This covalent coupling of the peptide hapten to the adjuvant can be effected in a manner which is well known in the state of the art. Reagents which are appropriate for this purpose comprise, in particular, N-succinimide esters, carbodiimides, EEDQ (N-ethoxy-carbonyl-2-ethoxy-1,2-dihydroquinoline) and the like.

The fragment of the P40 protein concerned, and the immunogenic element, can also be fused by means of genetic manipulation.

The fusion protein which is obtained between the fragment of the 40 protein and the immunogenic element can also be fused, by genetic manipulation, to a protein which is a receptor for a serum protein, in particular for human serum albumin.

The immunogenic element, an antigen or hapten, can, in particular, originate from viruses; those which may be mentioned are RSV (Respiratory Syncytial Virus) proteins or their fragments, for example protein G of RSV, or the hepatitis B antigen.

In the case of the RSV G protein, use may be made of the entire protein or of its fragments, where appropriate modified by point mutation or deletion.

The Applicant demonstrated that administration of a hapten coupled to a fragment of the P40 protein according to the invention resulted in a substantial increase in the immune response while limiting the risks of reactions against the adjuvant itself.

A process for increasing the immunogenicity of an antigen or of a hapten, characterized in that the said antigen or hapten is attached to an adjuvant which comprises all or part of the sequence of the P40 protein of *Klebsiella pneumoniae,* in the form of a complex as previously defined, is also part of the invention.

The invention also relates, therefore, to a vaccine, characterized in that it contains an immunogenic element attached to a fragment of the P40 protein which lacks a substantial part of the C-terminal sequence of the native P40 protein.

It also comprises pharmaceutical compositions which contain a complex which is formed between an adjuvant and an immunogenic element, as previously defined, and pharmaceutically acceptable excipients which are suited to administration of the complex by the parenteral and/or oral routes.

The invention also relates to the nucleotide sequences which encode the previously described peptides or proteins, and to the use of these sequences as a medicament. More particularly, such DNA sequences can be used in compositions which are intended for immunization by the intramuscular or intradermal route.

The examples which follow are intended to illustrate the invention without limiting its scope in any way.

Figure 2:
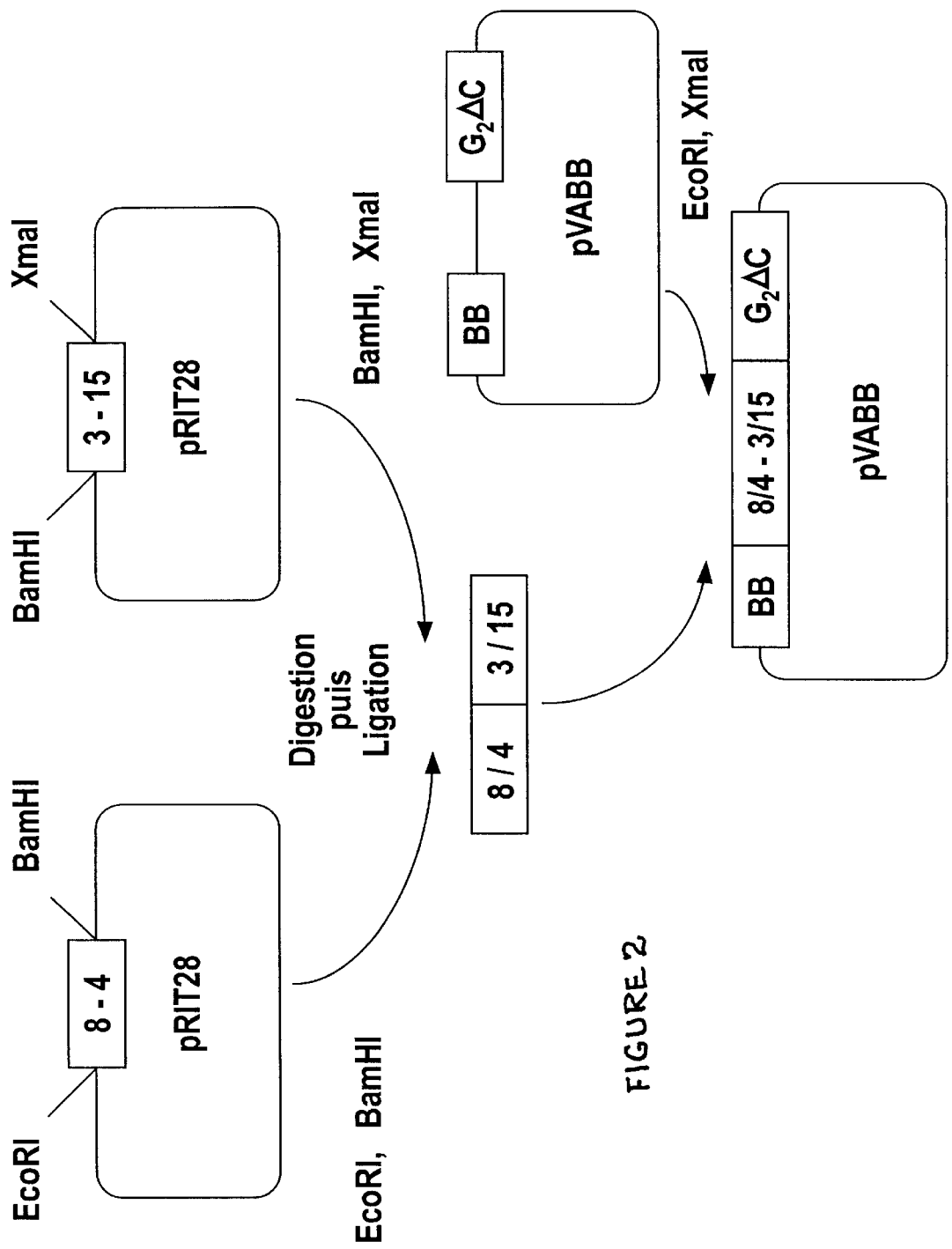
Figure 3:
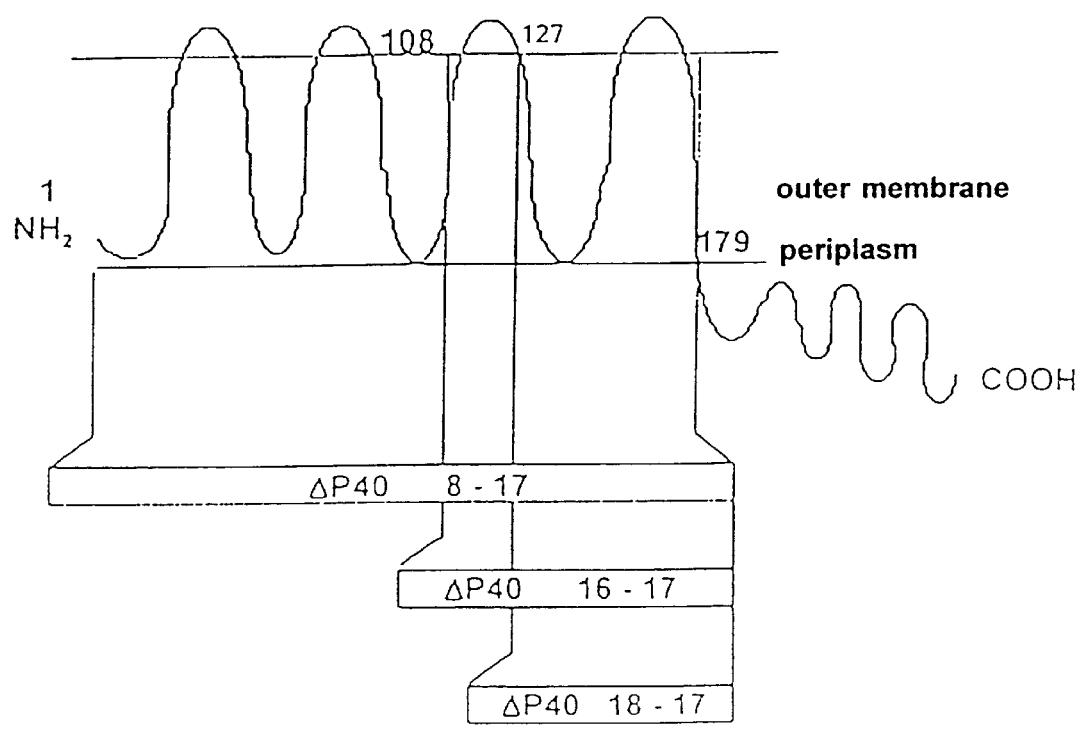
Figure 4:
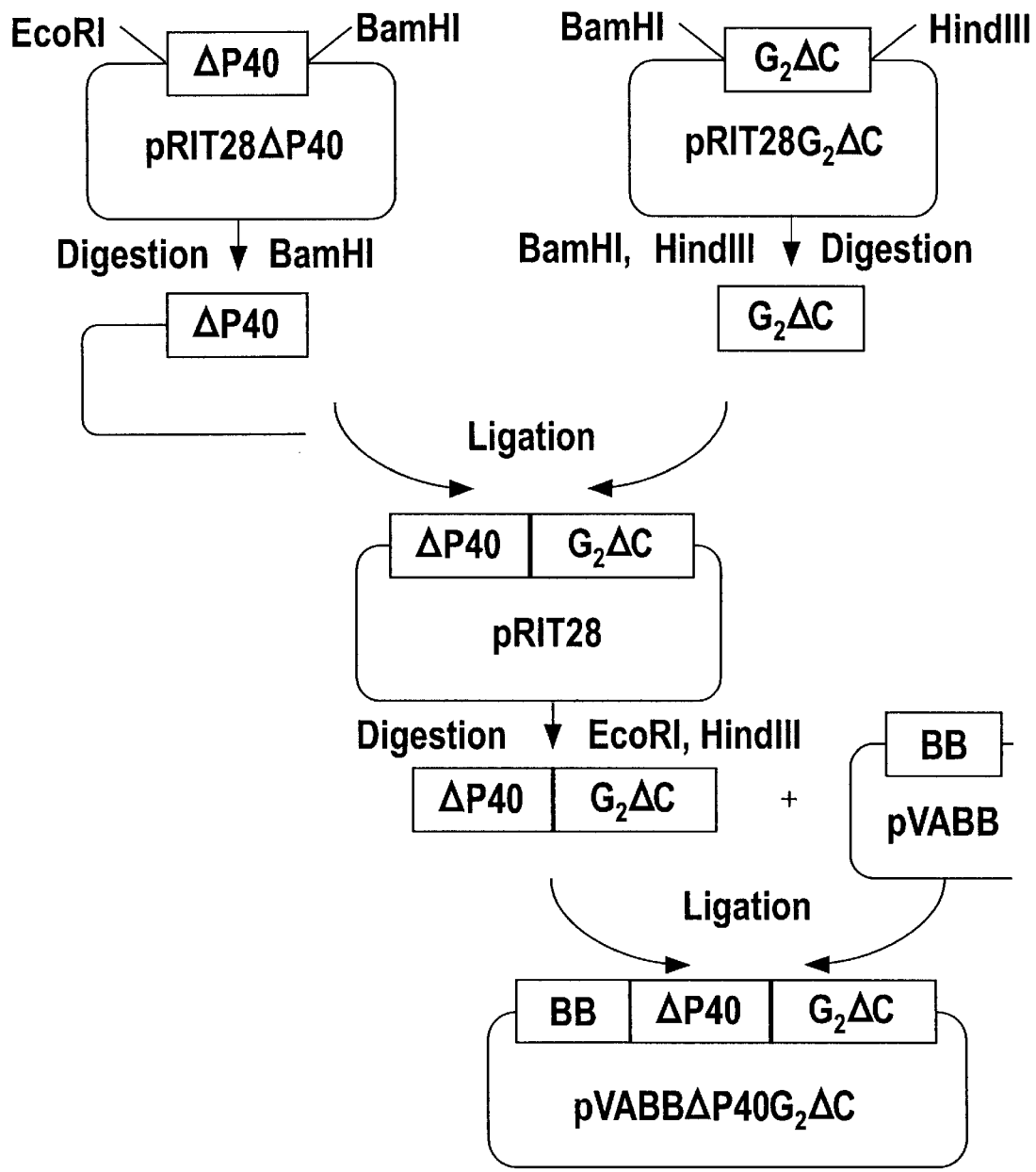
Figure 5:
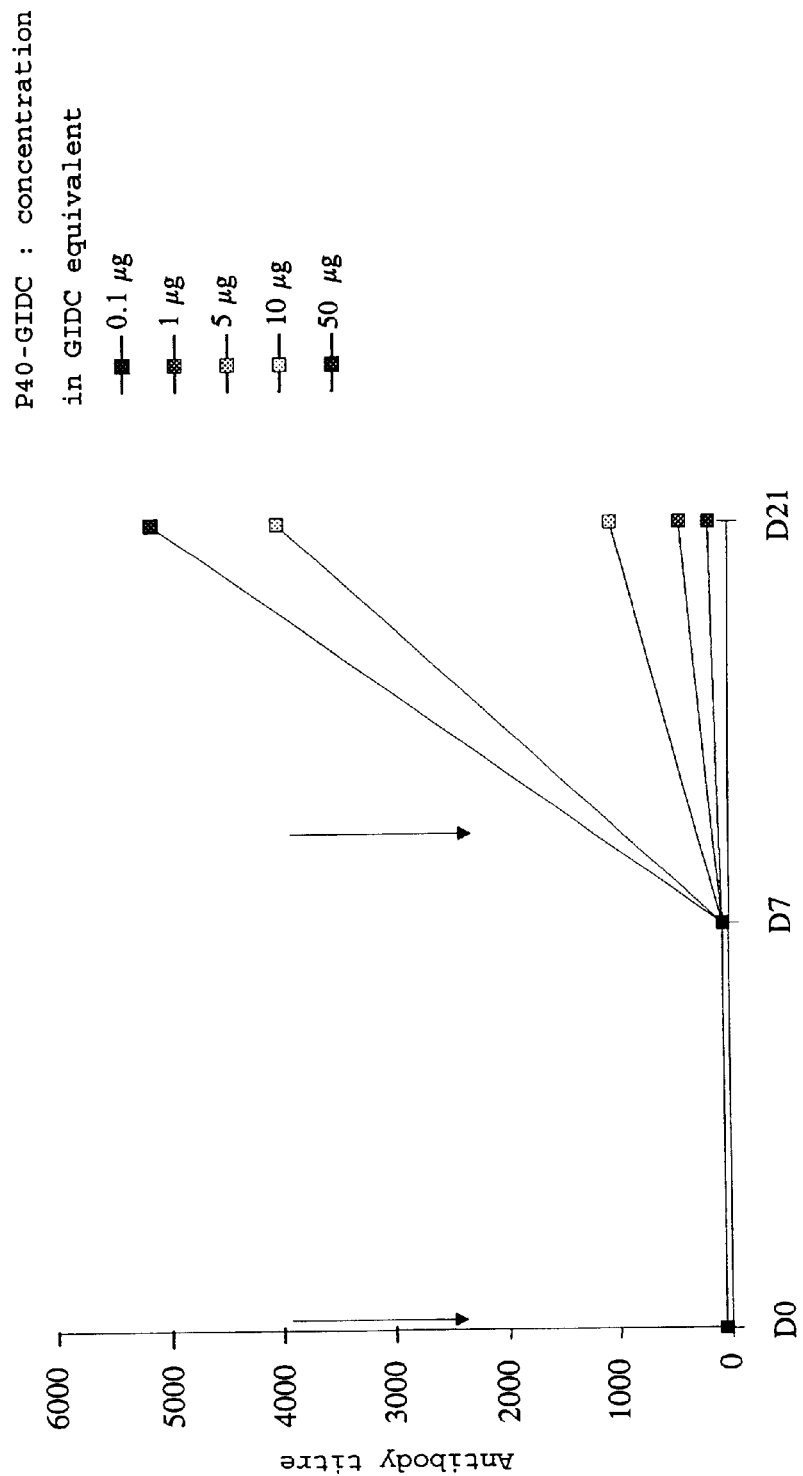
Figure 6:
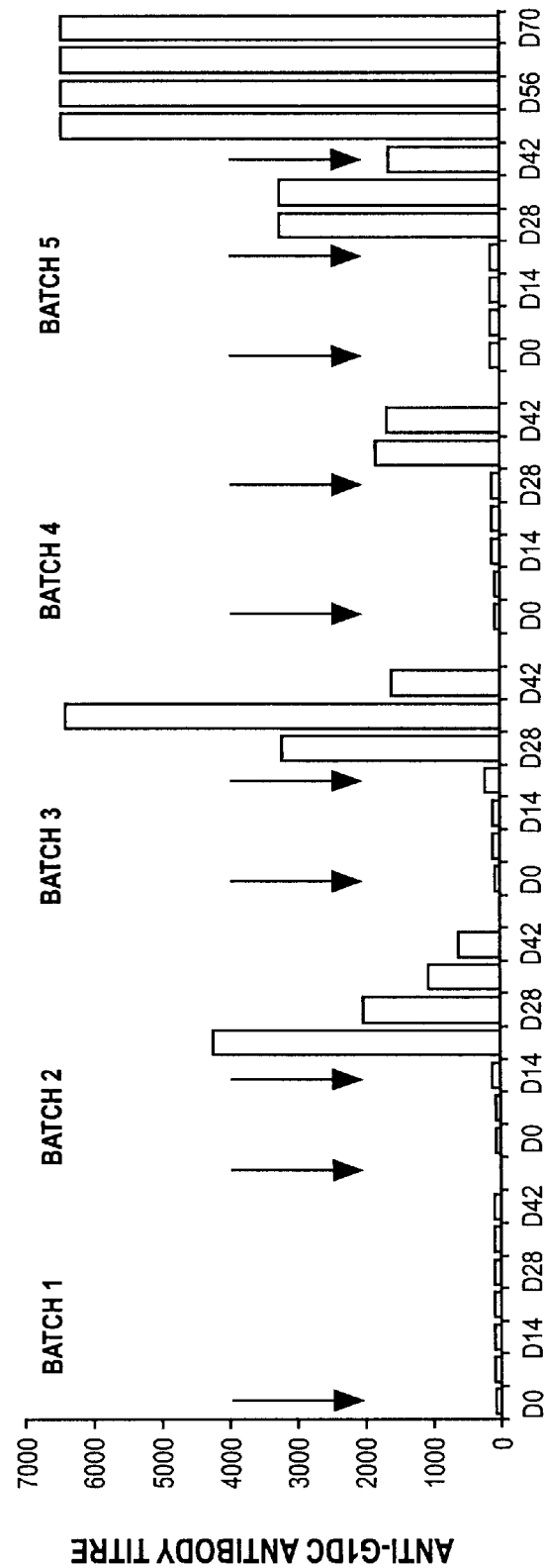

In these examples, reference will be made to the following figures:

FIG. 1: Strategy for cloning P40 by gene amplification.
FIG. 2: Cloning P40 into pVABBG2ΔC.
FIG. 3: Choice of the different P40 fragments.
FIG. 4: Cloning ΔP40G2ΔC into pVABB
FIG. 5: Anti-G1ΔC peptide antibody response following immunizations with different concentrations of P40ext-G1ΔC.
FIG. 6: Anti-G1ΔC peptide antibody response obtained using different immunization protocols.

EXAMPLE 1

Isolation and Purification of the p40 Protein
Material and Methods

*Klebsiella pneumoniae,* (strain I-145, 40 g of dry cells) biomass is adjusted to pH 2.5 with pure acetic acid.

After having added a ½ volume of a solution containing 6% cetrimide, 60% ethanol and 1.5 M $CaCl_2$, the pH of which is adjusted to 2.5 with acetic acid, the mixture is left to stir at room temperature for 16 hours.

After the mixture has been centrifuged at 15,000 g for 20 min and at 4° C., the proteins in the supernatant are precipitated with ethanol. Two consecutive precipitations, of 20 to 50% and then of 50 to 80%, are carried out with an intermediate centrifugation (10 min, 10,000 g, 4° C.).

The pellets obtained after the second precipitation are resuspended in a 1% solution of zwittergent 3-14.

After the mixture has been stirred at room temperature for 4 hours, its pH is adjusted to 6.5 using 1N NaOH.

Centrifugation of the mixture at 10,000 g for 20 min and at 4° C. yields a fraction which is enriched in membrane proteins (MP fraction).

The proteins of the MP fraction are dialysed against a 20 mM Tris/HCl, pH 8.0; 0.1% ZWITTERGENT 3-14 buffer, n-tetradecyl-N,N-dimethyl-3-ammonio-1-propane sulfate marketed by Calbiochem-Novabiochem Corp. The dialysate is loaded onto a column containing a support of the strong anion exchanger type (column of ⌀=50 mm×H=250 mm, Biorad MACROPREP® High Q gel) which is equilibrated in the above-described buffer. The P40 protein is eluted at an NaCl concentration of 50 mM in the equilibration buffer.

The fractions containing the P40 are pooled and dialysed against a 20 mM citrate, pH 3.0; 0.1% ZWITTERGENT 3-14 buffer. The dialysate is loaded onto a column containing a support of the strong cation exchanger type (dimensions of the column: ⌀=25 mm×H=160 mm, Biorad MACROPREP® High S gel) which is equilibrated in the 20 mM citrate, pH 3.0; 0.1% ZWITTERGENT 3-14 buffer. The P40 protein is eluted at an NaCl concentration of 0.7 M. The fractions containing the P40 are pooled and concentrated 30 by ultrafiltration using a MINITAN® Millipore tangential flow filtration system employing membrane discs having a cutoff threshold of 10 kDa marketed by Millipore Corp.

Results

The fractions obtained after each chromatographic step are analysed by SDS-PAGE in order to pool those which contain the P40 protein.

The protein quantities are measured by the Lowry method (Table 1).

TABLE 1

Table summarizing the quantities of protein and LPS in the fractions obtained in the different steps of the process for purifying the P40 protein (n.d. = not determined)

|  | Proteins | Yield | LPS |
|---|---|---|---|
| Biomass | 40 g | — | n.d. |
| MP fraction | 900 mg | 2.25% | n.d. |

TABLE 1-continued

Table summarizing the quantities of protein and
LPS in the fractions obtained in the different steps of
the process for purifying the P40 protein (n.d. = not
determined)

|  | Proteins | Yield | LPS |
|---|---|---|---|
| P40-enriched fraction | 400 mg | 1% | 10% |
| P40 protein | 130 mg | 0.3% | <1% |

The purity and homogeneity of the P40 protein are assessed by SDS-PAGE.

After the cation exchange chromatography step, the P40 protein is free of the main contaminant present in the MP fraction (the protein has an apparent molecular weight of 18 kDa) and is more than 95% pure. Moreover, this purification step eliminates the lipopolysaccharides. This purification step was not present in the purification process which was previously presented.

The electrophoretic profile of the P40 gives several bands. These bands are revealed after immunoblotting with mouse anti-P40 monoclonal antibodies. The upper major band corresponds to the denatured protein (by treatment at 100° C. for 15 min in the presence of SDS) and the lower minor band corresponds to the protein in its native form.

P40 is, therefore, a so-called heat-modifiable protein, and this property was checked by means of carrying out heating kinetics at 100° C. in the presence of SDS. Without heating, the protein in its native form has a β-sheet structure which fixes more SDS and which therefore migrates further towards the anode than does the denatured form (complete denaturation after 5 min at 100° C.), which exhibits an α-helical structure (Keller, K. B. 1978 J. Bacteriol., 134, 1181–1183).

Contamination with lipopolysaccharides (LPS) is assessed by gas-phase chromatographic measurement of β-hydroxymyristic acid, which is a marker fatty acid for *Klebsiella pneumoniae* LPS (Table 1).

This method can only be used to approximate the content of LPS in the samples derived from the different purification steps.

Since the quantity of β-hydroxymyristic acid which was present in the P40 fraction after cation exchange chromatography was less than the measurement threshold, the quantity of residual LPS may be estimated to be less than 1%.

EXAMPLE 2

Cloning and Expressing the P40 Protein

72% of the sequence of the OmpA gene of *Klebsiella pneumoniae* has been published by LAWRENCE et al., 1991, J. Gen. Microbiol., 137: 1911–1921).

The originality of our studies resides in determining all of the sequence, that is to say that corresponding to the 83 N-terminal amino acids and the 11 C-terminal amino acids (out of a total of 335 amino acids).

Material and Method
Bacterial Strains

*E. coli:* RV 308: strain ATCC 31608 (Maurer, R. et al., 1980, J. Mol. Biol., 139, 147–161).

*K. pneumoniae:* IP 145: strain C.I.B.P.F.—patent filed on Jan. 19, 1981.

Vectors pRIT 28 (Hultman T. et al., 1988, Nucléosides Nucléotides, 7: 629–638): cloning and sequencing vector which possesses the gene for resistance to ampicillin, the origins of replication of *E. coli* and phage F1 and a portion of the *E. coli* (β-galactosidase) lac Z gene.

*pVABB: Gene fusion expression vector.
Solutions
*Gene amplification

| Lysis buffer: | 25 mM Taps, pH 9.3 | |
| --- | --- | --- |
| | 2 mM MgCl$_2$ | |
| Amplication buffer: | 25 mM Taps, pH 9.3 | |
| | 2 mM MgCl$_2$ | |
| | 0.1% TWEEN 20, polyoxyethylene (2) - sorbitanemonolaureate marketed by Roche Molecular Biochemicals | |

*Purification of the proteins

| TST (20×): | Tris base | 0.5 M | |
| --- | --- | --- | --- |
| | HCl | 0.3 M | |
| | NaCl | 4 M | |
| | TWEEN 20 | 1% | |
| | EDTA | 20 mM | |
| Washing buffer: | Tris HCl | 50 mM | pH 8.5 |
| | MgCl$_2$ | 5 mM | |
| Denaturation solution: | Gua-HCl | 7.8 M | |
| | Tris-HCl | 28 mM | pH 8.5 |
| Renaturation solution: | Gua-HCl | 0.5 M | |
| | Tris-HCl | 25 mM | pH 8.5 |
| | NaCl | 150 mM | |
| | TWEEN 20 | 0.05%. | |

Synthesis of the Oligonucleotides

The choice of nucleotide primers was decided on the basis of the published part of the *Klebsiella pneumoniae* OMPA sequence (Lawrence, J. G. et al., 1991, J. Gen. Microbiol., 137: 1911–1921), the consensus sequence derived from aligning the sequences of 5 entero-bacteria (*E. coli, S. typhimurium, S. marcescens, S. dysenteriae* and *E. aeraginosae*) OMPAs, and peptide sequences which are obtained by manually sequencing.

The oligonucleotides were synthesized by the phosphoramidite chemical method on a "Gene Assembler Plus" appliance from Pharmacia.

PCR Gene Amplification of the P40 Gene

The DNA of the *Klebsiella pneumoniae* OMPA was amplified in the following manner.

A *Klebsiella pneumoniae* colony is lysed in 10 µl of lysis buffer by being heated at 95° C. for 5 minutes.

1 µl of this solution serves as the DNA source for the amplification rections.

These reactions are carried out in 100 µl of amplification buffer using 5 pmol of each primer and 1 unit of Taq polymerase enzyme (Perkin Elmer Cetus). Each cycle comprises one denaturation step of 30 seconds at 95° C., followed by hybridization of the primer to the DNA and an extension of one minute at 72° C. 30 cycles are performed in this way using a Perkin Elmer Cetus "Gen Amp PCR" 9000 thermocycler.

The subsequent PCRs are carried out using previously amplified DNA fragments.

The amplified DNA fragments are then digested and ligated to the pRIT 28 vector.

Sequencing

The fragments which have thus been cloned are sequenced on an Applied Biosystems 373 automated DNA Sequencer. The sequencing reactions are carried out using the "Dye Terminator" kit in accordance with the supplier's (Applied Biosystems) recommendations either on double-stranded DNA obtained after gene amplification or derived from a maxiprep, or on single-stranded DNA derived from denatured PCR fragments (Hultman, T. et al., 1989, Nucleid Acids Rev. 17: 4937–4946).

Expression of the Protein

The entire P40 gene is cloned into the expression vector pVABB. This vector renders it possible to affix a "BB" affinity tail to P40, with B being the part of the streptococcal G protein which binds serum albumin (Nygren, P. A. et al., 1988, J. Mol. Recognit. 1, 69–74).

The *E. coli* RV308 strains which have been transformed with the pVABBP40 vector are cultured, at 37° C., overnight and with stirring, in 100 ml of TSB which is supplemented with yeast extract, ampicillin (200 μg/ml), tetracycline (8 μg/ml) and tryptophan (100 μg/ml). On the following day, a culture of OD=1 at 580 nm wavelength is prepared in TSB+yeast extracts+amp+tet.

After culturing for 10 minutes, expression of the protein is induced by adding IAA (25 μg/ml) to the medium. The culture is centrifuged at 2460 g for 10 minutes at 4° C.

The pellet is taken up in 20 ml of 1×TST, pH 7.4, and the solution is then centrifuged at 23,000 g for 30 minutes at 4° C.

The supernatant is passed through HSA Sepharose, enabling the so-called soluble proteins to be isolated. The pellet is washed with washing buffer and then centrifuged at 23,000 g for 30 minutes at 4° C. The pellet containing the inclusion bodies is then taken up in 900 μl of a denaturing solution+100 μl of 10 mM dithiothreitol and this solution is incubated at 37° C. for 2 hours.

The solution is then incubated, at room temperature, overnight and with stirring, in 100 ml of renaturation buffer and then centrifuged at 23,000 g for 30 minutes at 4° C.

The supernatant is passed through HSA Sepharose.

In the two cases, the bound proteins are eluted with 0.5 M acetic acid, pH 2.8, and collected in 1 ml fractions.

The collected fractions are then analysed by SDS-PAGE gel electrophoresis and immunoblotting.

Results

The gene was cloned in three stages in accordance with the strategy depicted in FIG. 1.

In a first stage, we confirmed the published part of the sequence with the exception of a T in place of an A in position 103.

We then determined the 3' sequence of the gene and, after that, the 5' sequence.

The entire gene was obtained by fusing the two parts 8/4 and 3/14 and then cloned into the pRIT 28 vector. The sequence is sequence ID No. 1.

The protein is expressed in the BBP40 form.

It is mainly obtained from inclusion bodies. Some fifty milligrams of protein are purified from a 200 ml culture.

The electrophoretic profile demonstrates that BBP40, which is obtained after denaturation, is of high purity. The apparent molecular weight corresponds to the calculated theoretical weight, which is 63 kDa.

Immunoblot characterization demonstrates that the purified protein is well recognized by a rabbit anti-P40 serum.

EXAMPLE 3

BBP40G2ΔC Fusion Protein, Subgroup a

An oligonucleotide was synthesized which corresponded to the N-terminal part of the gene from which the stop codon had been deleted.

The 5' part was amplified by PCR, purified, cloned into the pRIT 28 vector, and sequenced by the method described in Example 2.

In a second stage, the two parts of the gene were fused and cloned into vector pVABBG2ΔC (FIG. 2). G2ΔC represents the sequence of a 101 amino acid fragment of the G protein of respiratory syncytial virus G (130–230).

*E. coli* bacteria of the RV308 strain are then transformed with the PVABBG2ΔC vector.

The proteins which are produced are purified as already described for BBP40.

Results

The BBP40G2ΔC protein is mainly obtained from the inclusion bodies. Some twelve mg of proteins are purified from 200 ml of culture medium.

The protein is fairly pure by electro-phoresis.

The apparent molecular weight corresponds to the calculated theoretical weight, which is 75 kDa.

EXAMPLE 4

Cloning and Expressing Three P40 Fragments

Material and Methods

The Oligonucleotides

Three oligonucleotides were synthesized which were complementary to the P40 sequence: 16–17–18 (cf. FIG. 3).

Defined parts of the gene were then amplified by PCR using the DNA from a miniprep (Applied protocol) of pRIT 28 P40.

In this way, it was possible to clone the part of the gene corresponding to all the transmembrane part (8/17, termed fragment No. 8) to two external loops and two transmembrane portions (16/17, termed fragment No. 16), and to 1 external loop and two transmembrane portions (18/17, termed fragment No. 18).

The DNA fragments which have thus been amplified are digested and then isolated and ligated into the pRIT 28 vector and sequenced (cf. BBP40 cloning of P40).

The BBΔP40G2ΔC Fusion Protein

The G2ΔC gene is isolated by digesting the vector pRIT 28 G2ΔC and then ligated into the digested vector pRIT 28 ΔP40 (ΔP40 represents one of the P40 fragments).

Subsequently, the entire ΔP40G2ΔC is isolated by digestion and cloned into pVABB (cf. FIG. 4).

The three hybrid proteins are expressed in accordance with the protocol described for BBP40.

Results

Just like BBP40 and BBP40G2ΔC, BB8G2ΔC is mainly obtained from the inclusion bodies. A 400 ml culture yields some ten mg of protein.

By contrast, most of the proteins BB18G2ΔC and BB16G2ΔC are present in the soluble form at the sonication step. In each case, some ten mg are obtained per 400 ml of culture.

These proteins were characterized by SDS-PAGE electrophoresis. Their molecular weight corresponds to the calculated theoretical weight:

BB8G2ΔC 58.03 kDa
BB16G2ΔC 46.5 kDa
BB18G2ΔC 45.5 kDa

In a Western blot, the three hybrids are recognized just as well by an anti-G2 polyclonal antibody as by anti-P40 antibody.

EXAMPLE 5

1. Effects of the P40 Protein on Cells of the Immune System 1.a. B Lymphocytes

30 μg of P40, obtained by extracting the membrane (P40 ext) or by genetic recombination (rec P40, i.e. BBP40), were injected subcutaneously into BALB/c mice (5 per group) on days 0 and 21. The immunizations were carried out without using any adjuvant. 10 days after the last immunization, the anti-P40ext antibody response was assessed in individual sera by the ELISA method. Table 2 gives the mean of the titres obtained on 5 samples. The negative controls did not contain any anti-P40ext antibody.

TABLE 2

Anti-P40ext antibody response

| Immunizations with: | xtP40 | recP40 |
|---|---|---|
| Antibody titres: | 87040 | 112640 |

Under these experimental conditions, the P40rec is as immunogenic as the P40ext. These two proteins therefore contain B epitopes which interact with the B lymphocytes.

1.b. T Lymphocytes

The delayed hypersensitivity reaction (HSR) to P40ext was measured by the deferred paw-pad swelling test. BALB/c mice (5 per group) were sensitized subcutaneously with 100 μg of P40ext without any adjuvant. After 6 to 10 days, the mice were stimulated subcutaneously with 100 μg of P40ext/20 μl in the right posterior paw pad while the left posterior paw pad was given PBS. The swelling of the paw pad was measured 24 hours later. No delayed hypersensitivity is observed in the negative control (5 non-sensitized mice).

TABLE 3

Delayed hypersensitivity reaction induced by p40ext, measured by swelling of the paw pad (in inm)

| D6 | | D10 | |
|---|---|---|---|
| BALB/c | C57B1/6 | BALB/c | C57B1/6 |
| 7.9 | 7.8 | 7.5 | 7.4 |

The results shown in Table 3 indicate that the mice immunized with P40ext produce highly quantitative delayed hypersensitivity reactions in the paw pad. The HSR reaction reflects the cell-mediated immune response, which requires Th1 cells. From this, it may be concluded that P40ext contains at least one T epitope which is able to promote the Th1 response, without MHC restriction.

1.3 Macrophages

The effect of P40ext on macrophages was determined by their production of nitrite. RAW 264.7 cells, which are mouse monocyte-macrophages, were incubated, at 37° C. for 72 hours, in the presence of different concentrations of P40ext. The quantities of nitrites in the supernatants of the cell cultures were measured by colorimetry using the Griess-Ilosvay reagent.

The production of nitrite reflects activation of the macrophages and plays a crucial role in the anti-microbial and anti-tumour activity of these cells. The data which were obtained show that P40ext stimulates the production of nitrite from RAW 264.7 cells, demonstrating that P40ext activates macrophages.

2. P40 is a Carrier, with an Adjuvant Effect, for a Peptide (G1ΔC)

2.1. Comparison of P40ext with Other Supports

The peptide which is used is G1ΔC, which is a peptide obtained from protein G of RSV: (G174–187 ΔC) Trudel et al., 1991, J. Virol. 185: 749–757.

Kinetics of the Immune Response to G1 ΔC

C57B1/6 mice (5 per group) are immunized with different forms of G1 ΔC in accordance with an identical immunization protocol. The antibody responses induced by the different forms of G1 ΔC are compared at times of 7, 17, 28, 35 and 42 days after the start of the experiment.

The anti-G1 ΔC response is significantly greater and more rapid when the mice are immunized with P40/G1 ΔC than when they are immunized in the more conventional way with TT/G1 ΔC or KLH/G1 ΔC+FA. A single injection of P40/G1 ΔC results, in 7 days, in an anti-G1 ΔC antibody titre of 1000. With TT/G1 ΔC+FA, this titre is obtained in 28 days. The maximum response (titre=1/380000), obtained after three injections, in 28 days, is approximately 30 times greater than that obtained with KLH/G1 ΔC+FA, and 70 times greater than that obtained with TT/G1 ΔC. The anti-G1 antibody titre persists, without diminishing, up to day 42.

Conclusion

Chemically coupling the G1 ΔC peptide to the P40 protein rendered it possible to induce an anti-G1 ΔC response which was as great as that obtained with the KLH/G1 ΔC+FA or TT/G1 ΔC reference models.

The results obtained demonstrate that P40ext is a carrier molecule for G1ΔC which has an adjuvant effect: P40ext is superior to tetanus toxin and as good as the combination KLH+Freund's adjuvant.

2.1. Isotype Distribution of the Anti-G1ΔC Peptide Antibodies

The isotypes of the sera obtained during the above-described experiments were determined by ELISA. Table 4 gives the means of the A450 values of 5 individual sera which were tested at a dilution of 1/250.

TABLE 4

Isotype distribution of the anti-G1ΔC peptide antibodies

| | IgG1 | IgG2a | IgG2b | IgG3 |
|---|---|---|---|---|
| A450 (dil. 1/250) | 2.892 | 1.212 | 2.970 | 0.209 |

It has been shown that the secretion of antibody isotype is regulated by subsets of antigen-specific Th cells, which can be divided into two subsets, Th1 and Th2. The Th1 clones produce IL-2 and IFN gamma and lymphotoxins, while the Th2 clones produce IL-4 and IL-5. The Th1 and Th2 clones specifically induce the secretion of IgG2a+IgG3 and IgG1+IgG2b+IgE, respectively, by antigen-specific B cells. The data presented in Table 4 show that IgG1 and IgG2b are the two main isotypes of anti-G1ΔC antibodies, with IgG2a also being represented. It may be concluded that, in C57B1/6 mice, P40-G1ΔC provokes a Th2 response which is greater than the Th1 response.

2.2 Dose-effect Study

Different concentrations of P40ext-G1ΔC were injected subcutaneously, on days 0, 10 and 21, into BALB/c mice (5 per group). One week after the last immunization, blood samples are withdrawn and the anti-G1ΔC peptide antibody response is measured by ELISA in the individual sera. The mean of the titres of 5 samples is calculated.

FIG. 5 shows the dose-effect relationship for P40ext-G1ΔC. An anti-G1ΔC peptide antibody response is obtained with 1 μg of P40ext-G1ΔC. The highest antibody titres are observed with 10 to 50 μg of P40ext-G1ΔC.

2.4 Determination of the Optimum Immunization Protocol

P40ext-G1ΔC (equivalent to 10 μg of G1ΔC) was injected subcutaneously, on the days indicated in FIG. 6, into BALB/c mice (5 per group). The anti-G1ΔC peptide antibody response is measured by ELISA on the individual sera. 4 immunization protocols were tested: one injection, two injections on days 0 and 14, or on days 0 and 21, and three injections on days 0, 21 and 40. The greatest anti-G1ΔC peptide antibody response is obtained with three injections.

3. P40ext is an Efficient Adjuvant for a Protein Antigen (BBG2ΔC)

BBG2ΔC conjugated chemically with P40ext (equivalent to 10 Δg of G2ΔC) was injected subcutaneously, on days 0 and 21, into BALB/c mice (5 per group). Ten days later, the anti-G2ΔC antibody response is measured by ELISA in the individual sera. The means of the titres of 5 samples are given in Table 5. The negative control did not contain anti-G2ΔC antibody.

TABLE 5

Adjuvant effect of P40ext on a protein antigen

|  | Anti-G2ΔC antibody titre |
|---|---|
| BBG2ΔC | 160 |
| BBG2ΔC + Freund's adjuvant | 2051200 |
| extP40-BBG2ΔC | 29800 |

BBG2ΔC is weakly immunogenic. Using Freund's adjuvant increases the titre of anti-G2ΔC antibody. When BBG2ΔC is conjugated chemically to P40ext, the anti-G2ΔC antibody response is increased approximately 200-fold. Therefore, P40ext is a good adjuvant for a protein antigen.

4. Adjuvant Activity of P40 Fragments

BALB/c mice (5 per group) were injected subcutaneously on day 0, and stimulated on day 21, with the following recombinant proteins: fusion protein BBP40G2ΔC, the fusion protein containing P40 fragment No. 8 (BB8G2ΔC), the fusion protein containing P40 fragment No. 16 (BB16G2ΔC) and the fusion protein containing P40 fragment No. 18 (BB18G2ΔC) (equivalent to 10 μg of G2ΔC).

On day 31, the anti-G2ΔC, anti-P40 and anti-BB antibody responses are measured by ELISA in the individual sera. The means of the titres of 5 individual sera are calculated. The negative controls did not contain anti-G2ΔC antibody.

TABLE 6

Adjuvant effect of the recombinant P40 fragments

|  | TITRE OF ANTI-G2ΔC ANTIBODY | TITRE OF ANTI-BB ANTIBODY | TITRE OF ANTI-P40 ANTIBODY |
|---|---|---|---|
| BBP40G2ΔC | 14 800 | 266 240 | 450 506 |
| BB8G2ΔC | 7 400 | 430 080 | 56 640 |
| BB16G2ΔC | 1 800 | 84 480 | 880 |
| BB18G2ΔC | 1 360 | 184 320 | 240 |

This experiment shows that the P40 fragments retain the properties of the complete protein. This is particularly striking when the anti-BB antibody response is considered.

The anti-P40 antibody response is considerably reduced when fragments of P40 are used.

---

What is claimed is:

1. An isolated adjuvant comprising at least a fragment of the P40 protein of *Klebsiella pneumoniae,* said fragment having the amino acid sequence of SEQ ID NO: 8.

2. The adjuvant of claim 1 having the amino acid sequence of SEQ ID NO: 2.

3. The adjuvant of claim 1 having the amino acid sequence of SEQ ID NO: 4.

4. The adjuvant of claim 1 having the amino acid sequence of SEQ ID NO: 6.

5. The adjuvant of claim 1 having the amino acid sequence of SEQ ID NO: 8.

6. An immunogenic complex comprising an antigen or hapten attached to the adjuvant of claim 1.

7. The immunogenic complex of claim 6, wherein said antigen or hapten is attached to said adjuvant by a covalent bond.

8. The immunogenic complex of claim 6 wherein said antigen or hapten is an immunogenic fragment of the G protein of Respiratory Syncytial Virus.

9. The immunogenic complex of claim 6 wherein said antigen or hapten is fused to a protein which is a receptor for a serum protein.

10. A vaccine comprising the immunogenic complex of claim 6 and a pharmaceutically acceptable carrier.

11. The immunogenic complex of claim 9 wherein said serum protein is human serum albumin.

\* \* \* \* \*

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1007 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1007

(xi) SEQUENCE DESCRIPTION: SEQ ID NO: 1:

```
GCT CCG AAA GAT AAC ACC TGG TAT GCA GGT GGT AAA CTG GGT TGG TCC      48
Ala Pro Lys Asp Asn Thr Trp Tyr Ala Gly Gly Lys Leu Gly Trp Ser
 1               5                  10                  15

CAG TAT CAC GAC ACC GGT TTC TAC GGT AAC GGT TTC CAG AAC AAC AAC      96
Gln Tyr His Asp Thr Gly Phe Tyr Gly Asn Gly Phe Gln Asn Asn Asn
            20                  25                  30
```

-continued

| | | |
|---|---|---|
| GGT CCG ACC CGT AAC GAT CAG CTT GGT GCT GGT GCG TTC GGT GGT TAC<br>Gly Pro Thr Arg Asn Asp Gln Leu Gly Ala Gly Ala Phe Gly Gly Tyr<br>         35                             40                          45 | 144 |

```
GGT CCG ACC CGT AAC GAT CAG CTT GGT GCT GGT GCG TTC GGT GGT TAC      144
Gly Pro Thr Arg Asn Asp Gln Leu Gly Ala Gly Ala Phe Gly Gly Tyr
         35                  40                  45

CAG GTT AAC CCG TAC CTC GGT TTC GAA ATG GGT TAT GAC TGG CTG GGC      192
Gln Val Asn Pro Tyr Leu Gly Phe Glu Met Gly Tyr Asp Trp Leu Gly
 50                  55                  60

CGT ATG GCA TAT AAA GGC AGC GTT GAC AAC GGT GCT TTC AAA GCT CAG      240
Arg Met Ala Tyr Lys Gly Ser Val Asp Asn Gly Ala Phe Lys Ala Gln
 65              70                  75                  80

GGC GTT CAG CTG ACC GCT AAA CTG GGT TAC CCG ATC ACT GAC GAT CTG      288
Gly Val Gln Leu Thr Ala Lys Leu Gly Tyr Pro Ile Thr Asp Asp Leu
             85                  90                  95

GAC ATC TAC ACC CGT CTG GGC GGC ATG GTT TGG CGC GCT GAC TCC AAA      336
Asp Ile Tyr Thr Arg Leu Gly Gly Met Val Trp Arg Ala Asp Ser Lys
100                 105                 110

GGC AAC TAC GCT TCT ACC GGC GTT TCC CGT AGC GAA CAC GAC ACT GGC      384
Gly Asn Tyr Ala Ser Thr Gly Val Ser Arg Ser Glu His Asp Thr Gly
                115                 120                 125

GTT TCC CCA GTA TTT GCT GGC GGC GTA GAG TGG GCT GTT ACT CGT GAC      432
Val Ser Pro Val Phe Ala Gly Gly Val Glu Trp Ala Val Thr Arg Asp
130                 135                 140

ATC GCT ACC CGT CTG GAA TAC CAG TGG GTT AAC AAC ATC GGC GAC GCG      480
Ile Ala Thr Arg Leu Glu Tyr Gln Trp Val Asn Asn Ile Gly Asp Ala
145                 150                 155                 160

GGC ACT GTG GGT ACC CGT CCT GAT AAC GGC ATG CTG AGC CTG GGC GTT      528
Gly Thr Val Gly Thr Arg Pro Asp Asn Gly Met Leu Ser Leu Gly Val
                165                 170                 175

TCC TAC CGC TTC GGT CAG GAA GAT GCT GCA CCG GTT GTT GCT CCG GCT      576
Ser Tyr Arg Phe Gly Gln Glu Asp Ala Ala Pro Val Val Ala Pro Ala
            180                 185                 190

CCG GCT CCG GCT CCG GAA GTG GCT ACC AAG CAC TTC ACC CTG AAG TCT      624
Pro Ala Pro Ala Pro Glu Val Ala Thr Lys His Phe Thr Leu Lys Ser
        195                 200                 205

GAC GTT CTG TTC AAC TTC AAC AAA GCT ACC CTG AAA CCG GAA GGT CAG      672
Asp Val Leu Phe Asn Phe Asn Lys Ala Thr Leu Lys Pro Glu Gly Gln
    210                 215                 220

CAG GCT CTG GAT CAG CTG TAC ACT CAG CTG AGC AAC ATG GAT CCG AAA      720
Gln Ala Leu Asp Gln Leu Tyr Thr Gln Leu Ser Asn Met Asp Pro Lys
225                 230                 235                 240

GAC GGT TCC GCT GTT GTT CTG GGC TAC ACC GAC CGC ATC GGT TCC GAA      768
Asp Gly Ser Ala Val Val Leu Gly Tyr Thr Asp Arg Ile Gly Ser Glu
                245                 250                 255

GCT TAC AAC CAG CAG CTG TCT GAG AAA CGT GCT CAG TCC GTT GTT GAC      816
Ala Tyr Asn Gln Gln Leu Ser Glu Lys Arg Ala Gln Ser Val Val Asp
            260                 265                 270

TAC CTG GTT GCT AAA GGC ATC CCG GCT GGC AAA ATC TCC GCT CGC GGC      864
Tyr Leu Val Ala Lys Gly Ile Pro Ala Gly Lys Ile Ser Ala Arg Gly
        275                 280                 285

ATG GGT GAA TCC AAC CCG GTT ACT GGC AAC ACC TGT GAC AAC GTG AAA      912
Met Gly Glu Ser Asn Pro Val Thr Gly Asn Thr Cys Asp Asn Val Lys
    290                 295                 300

GCT CGC GCT GCC CTG ATC GAT TGC CTG GCT CCG GAT CGT CGT GTA GAG      960
Ala Arg Ala Ala Leu Ile Asp Cys Leu Ala Pro Asp Arg Arg Val Glu
305                 310                 315                 320

ATC GAA GTT AAA GGC TAC AAA GAA GTT GTA ACT CAG CCG GCG GGT TA      1007
Ile Glu Val Lys Gly Tyr Lys Glu Val Val Thr Gln Pro Ala Gly
                325                 330                 335
```

-continued (2) INFORMATION FOR SEQ ID NO: 2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO: 2:

```
Ala Pro Lys Asp Asn Thr Trp Tyr Ala Gly Gly Lys Leu Gly Trp Ser
 1               5                  10                  15

Gln Tyr His Asp Thr Gly Phe Tyr Gly Asn Gly Phe Gln Asn Asn Asn
                20                  25                  30

Gly Pro Thr Arg Asn Asp Gln Leu Gly Ala Gly Ala Phe Gly Gly Tyr
            35                  40                  45

Gln Val Asn Pro Tyr Leu Gly Phe Glu Met Gly Tyr Asp Trp Leu Gly
 50                  55                  60

Arg Met Ala Tyr Lys Gly Ser Val Asp Asn Gly Ala Phe Lys Ala Gln
 65                  70                  75                  80

Gly Val Gln Leu Thr Ala Lys Leu Gly Tyr Pro Ile Thr Asp Asp Leu
                85                  90                  95

Asp Ile Tyr Thr Arg Leu Gly Gly Met Val Trp Arg Ala Asp Ser Lys
            100                 105                 110

Gly Asn Tyr Ala Ser Thr Gly Val Ser Arg Ser Glu His Asp Thr Gly
            115                 120                 125

Val Ser Pro Val Phe Ala Gly Gly Val Glu Trp Ala Val Thr Arg Asp
 130                 135                 140

Ile Ala Thr Arg Leu Glu Tyr Gln Trp Val Asn Asn Ile Gly Asp Ala
 145                 150                 155                 160

Gly Thr Val Gly Thr Arg Pro Asp Asn Gly Met Leu Ser Leu Gly Val
                165                 170                 175

Ser Tyr Arg Phe Gly Gln Glu Asp Ala Ala Pro Val Val Ala Pro Ala
            180                 185                 190

Pro Ala Pro Ala Pro Glu Val Ala Thr Lys His Phe Thr Leu Lys Ser
            195                 200                 205

Asp Val Leu Phe Asn Phe Asn Lys Ala Thr Leu Lys Pro Glu Gly Gln
 210                 215                 220

Gln Ala Leu Asp Gln Leu Tyr Thr Gln Leu Ser Asn Met Asp Pro Lys
 225                 230                 235                 240

Asp Gly Ser Ala Val Leu Gly Tyr Thr Asp Arg Ile Gly Ser Glu
                245                 250                 255

Ala Tyr Asn Gln Gln Leu Ser Glu Lys Arg Ala Gln Ser Val Val Asp
            260                 265                 270

Tyr Leu Val Ala Lys Gly Ile Pro Ala Gly Lys Ile Ser Ala Arg Gly
            275                 280                 285

Met Gly Glu Ser Asn Pro Val Thr Gly Asn Thr Cys Asp Asn Val Lys
            290                 295                 300

Ala Arg Ala Ala Leu Ile Asp Cys Leu Ala Pro Asp Arg Arg Val Glu
 305                 310                 315                 320

Ile Glu Val Lys Gly Tyr Lys Glu Val Val Thr Gln Pro Ala Gly
                325                 330                 335
```

(2) INFORMATION FOR SEQ ID NO: 3:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..537

(xi) SEQUENCE DESCRIPTION: SEQ ID NO: 3:

```
GCT CCG AAA GAT AAC ACC TGG TAT GCA GGT GGT AAA CTG GGT TGG TCC      48
Ala Pro Lys Asp Asn Thr Trp Tyr Ala Gly Gly Lys Leu Gly Trp Ser
 1               5                  10                  15

CAG TAT CAC GAC ACC GGT TTC TAC GGT AAC GGT TTC CAG AAC AAC AAC      96
Gln Tyr His Asp Thr Gly Phe Tyr Gly Asn Gly Phe Gln Asn Asn Asn
                20                  25                  30

GGT CCG ACC CGT AAC GAT CAG CTT GGT GCT GGT GCG TTC GGT GGT TAC     144
Gly Pro Thr Arg Asn Asp Gln Leu Gly Ala Gly Ala Phe Gly Gly Tyr
            35                  40                  45

CAG GTT AAC CCG TAC CTC GGT TTC GAA ATG GGT TAT GAC TGG CTG GGC     192
Gln Val Asn Pro Tyr Leu Gly Phe Glu Met Gly Tyr Asp Trp Leu Gly
        50                  55                  60

CGT ATG GCA TAT AAA GGC AGC GTT GAC AAC GGT GCT TTC AAA GCT CAG     240
Arg Met Ala Tyr Lys Gly Ser Val Asp Asn Gly Ala Phe Lys Ala Gln
 65                  70                  75                  80

GGC GTT CAG CTG ACC GCT AAA CTG GGT TAC CCG ATC ACT GAC GAT CTG     288
Gly Val Gln Leu Thr Ala Lys Leu Gly Tyr Pro Ile Thr Asp Asp Leu
                85                  90                  95

GAC ATC TAC ACC CGT CTG GGC GGC ATG GTT TGG CGC GCT GAC TCC AAA     336
Asp Ile Tyr Thr Arg Leu Gly Gly Met Val Trp Arg Ala Asp Ser Lys
            100                 105                 110

GGC AAC TAC GCT TCT ACC GGC GTT TCC CGT AGC GAA CAC GAC ACT GGC     384
Gly Asn Tyr Ala Ser Thr Gly Val Ser Arg Ser Glu His Asp Thr Gly
        115                 120                 125

GTT TCC CCA GTA TTT GCT GGC GGC GTA GAG TGG GCT GTT ACT CGT GAC     432
Val Ser Pro Val Phe Ala Gly Gly Val Glu Trp Ala Val Thr Arg Asp
130                 135                 140

ATC GCT ACC CGT CTG GAA TAC CAG TGG GTT AAC AAC ATC GGC GAC GCG     480
Ile Ala Thr Arg Leu Glu Tyr Gln Trp Val Asn Asn Ile Gly Asp Ala
145                 150                 155                 160

GGC ACT GTG GGT ACC CGT CCT GAT AAC GGC ATG CTG AGC CTG GGC GTT     528
Gly Thr Val Gly Thr Arg Pro Asp Asn Gly Met Leu Ser Leu Gly Val
                165                 170                 175

TCC TAC CGC                                                          537
Ser Tyr Arg
```

(2) INFORMATION FOR SEQ ID NO: 4:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO: 4:

```
Ala Pro Lys Asp Asn Thr Trp Tyr Ala Gly Gly Lys Leu Gly Trp Ser
 1               5                  10                  15
```

-continued

```
Gln Tyr His Asp Thr Gly Phe Tyr Gly Asn Gly Phe Gln Asn Asn Asn
             20                  25                  30

Gly Pro Thr Arg Asn Asp Gln Leu Gly Ala Gly Ala Phe Gly Gly Tyr
         35                  40                  45

Gln Val Asn Pro Tyr Leu Gly Phe Glu Met Gly Tyr Asp Trp Leu Gly
 50                  55                  60

Arg Met Ala Tyr Lys Gly Ser Val Asp Asn Gly Ala Phe Lys Ala Gln
 65                  70                  75                  80

Gly Val Gln Leu Thr Ala Lys Leu Gly Tyr Pro Ile Thr Asp Asp Leu
             85                  90                  95

Asp Ile Tyr Thr Arg Leu Gly Gly Met Val Trp Arg Ala Asp Ser Lys
            100                 105                 110

Gly Asn Tyr Ala Ser Thr Gly Val Ser Arg Ser Glu His Asp Thr Gly
            115                 120                 125

Val Ser Pro Val Phe Ala Gly Gly Val Glu Trp Ala Val Thr Arg Asp
130                 135                 140

Ile Ala Thr Arg Leu Glu Tyr Gln Trp Val Asn Asn Ile Gly Asp Ala
145                 150                 155                 160

Gly Thr Val Gly Thr Arg Pro Asp Asn Gly Met Leu Ser Leu Gly Val
            165                 170                 175

Ser Tyr Arg
```

(2) INFORMATION FOR SEQ ID NO: 5:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..216

(xi) SEQUENCE DESCRIPTION: SEQ ID NO: 5:

```
CGC GCT GAC TCC AAA GGC AAC TAC GCT TCT ACC GGC GTT TCC CGT AGC      48
Arg Ala Asp Ser Lys Gly Asn Tyr Ala Ser Thr Gly Val Ser Arg Ser
 1               5                  10                  15

GAA CAC GAC ACT GGC GTT TCC CCA GTA TTT GCT GGC GGC GTA GAG TGG      96
Glu His Asp Thr Gly Val Ser Pro Val Phe Ala Gly Gly Val Glu Trp
             20                  25                  30

GCT GTT ACT CGT GAC ATC GCT ACC CGT CTG GAA TAC CAG TGG GTT AAC     144
Ala Val Thr Arg Asp Ile Ala Thr Arg Leu Glu Tyr Gln Trp Val Asn
 35                  40                  45

AAC ATC GGC GAC GCG GGC ACT GTG GGT ACC CGT CCT GAT AAC GGC ATG     192
Asn Ile Gly Asp Ala Gly Thr Val Gly Thr Arg Pro Asp Asn Gly Met
             50                  55                  60

CTG AGC CTG GGC GTT TCC TAC CGC                                     216
Leu Ser Leu Gly Val Ser Tyr Arg
 65                  70
```

(2) INFORMATION FOR SEQ ID NO: 6:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 6:

Arg Ala Asp Ser Lys Gly Asn Tyr Ala Ser Thr Gly Val Ser Arg Ser
 1               5                  10                  15

Glu His Asp Thr Gly Val Ser Pro Val Phe Ala Gly Gly Val Glu Trp
                20                  25                  30

Ala Val Thr Arg Asp Ile Ala Thr Arg Leu Glu Tyr Gln Trp Val Asn
            35                  40                  45

Asn Ile Gly Asp Ala Gly Thr Val Gly Thr Arg Pro Asp Asn Gly Met
        50                  55                  60

Leu Ser Leu Gly Val Ser Tyr Arg
65                  70

(2) INFORMATION FOR SEQ ID NO: 7:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 7:

ACT GGC GTT TCC CCA GTA TTT GCT GGC GGC GTA GAG TGG GCT GTT ACT        48
Thr Gly Val Ser Pro Val Phe Ala Gly Gly Val Glu Trp Ala Val Thr
 1               5                  10                  15

CGT GAC ATC GCT ACC CGT CTG GAA TAC CAG TGG GTT AAC AAC ATC GGC        96
Arg Asp Ile Ala Thr Arg Leu Glu Tyr Gln Trp Val Asn Asn Ile Gly
                20                  25                  30

GAC GCG GGC ACT GTG GGT ACC CGT CCT GAT AAC GGC ATG CTG AGC CTG       144
Asp Ala Gly Thr Val Gly Thr Arg Pro Asp Asn Gly Met Leu Ser Leu
            35                  40                  45

GGC GTT TCC TAC CGC                                                   159
Gly Val Ser Tyr Arg
    50

(2) INFORMATION FOR SEQ ID NO: 8:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 8:

Thr Gly Val Ser Pro Val Phe Ala Gly Gly Val Glu Trp Ala Val Thr
 1               5                  10                  15

Arg Asp Ile Ala Thr Arg Leu Glu Tyr Gln Trp Val Asn Asn Ile Gly
                20                  25                  30

Asp Ala Gly Thr Val Gly Thr Arg Pro Asp Asn Gly Met Leu Ser Leu
            35                  40                  45

Gly Val Ser Tyr Arg
    50